United States Patent [19]

Valentine et al.

[11] Patent Number: 5,387,206
[45] Date of Patent: Feb. 7, 1995

[54] MECHANICAL TREATMENT OF DRY SPONGE MATERIAL TO IMPART FLEXIBILITY

[75] Inventors: Douglas R. Valentine, Oakdale, Conn.; Arthur A. Gertzman, Bridgewater, N.J.

[73] Assignee: Merocel Corporation, Mystic, Conn.

[21] Appl. No.: 112,462

[22] Filed: Aug. 27, 1993

[51] Int. Cl.[6] ............... A61F 13/15; A61F 13/20
[52] U.S. Cl. .................... 604/358; 604/380; 604/383; 604/385.1; 604/904; 128/851
[58] Field of Search ............. 128/846, 849, 853, 854, 128/855; 604/358, 369, 379, 380, 382, 383, 384, 385.1, 904

[56] References Cited

U.S. PATENT DOCUMENTS

| | | | |
|---|---|---|---|
| 2,952,259 | 9/1960 | Burgeni | 604/380 |
| 2,952,260 | 9/1960 | Burgeni | 604/380 |
| 3,924,627 | 12/1975 | Nystrand | 604/380 |
| 4,389,211 | 6/1983 | Lenaghan | 604/383 |
| 4,758,240 | 7/1988 | Glassman | 604/379 |

FOREIGN PATENT DOCUMENTS

| | | | |
|---|---|---|---|
| 2704817 | 8/1978 | Germany | 604/385.1 |
| 862884 | 3/1961 | United Kingdom | 604/380 |

*Primary Examiner*—Randall L. Green
*Assistant Examiner*—P. Zuttarelli
*Attorney, Agent, or Firm*—Gipple & Hale

[57] ABSTRACT

A medical sponge comprising a sterile rigid absorbent linearly shaped sponge body, one end of the body being rounded. A plurality of parallel flex lines are formed in said linear body running substantially along its length with one section of the body having flex lines formed therein which run perpendicular to and intersect the parallel flex lines. An end of the body is provided with angular flex lines formed therein which run angularly to and intersect the parallel flex lines.

24 Claims, 2 Drawing Sheets

MECHANICAL TREATMENT OF DRY SPONGE MATERIAL TO IMPART FLEXIBILITY

BACKGROUND OF THE INVENTION

The present invention generally relates to treating sponge material to impart flexibility to the sponge material and, more particularly, to mechanically treat a rigid absorbent compressed dry sponge material to impart flexibility to the material allowing it to be easily inserted into a wound or other cavity.

A common means for mechanically imparting flexibility to sponge and other absorbent materials has been to apply variable compression to the material so that different points within the absorbent material receive little or no compression while other points receive significant or complete compression.

The method of rippling an absorbent material to provide a flexibility or softness is well known in the art. In U.S. Pat. No. 4,559,050 a non-woven web of synthetic wet resilient fibers is microcorrugated to provide a Taber stiffness value of about 25 or less. The microcorrugating process consists of passing the web through fluted intermeshing rolls having sufficient pressure to fracture and form cross-directional hinge lines. The lines found in the fibrous web product are in the machine direction thus providing hinge lines in the machine direction. The microcorrugations in the fibrous web result in a softness and flexibility imparted to an otherwise stiff material without a substantial loss of tensile strength. The fibrous web can be formed from synthetic staple fibers such as polyethylene, polypropylene, polyester, nylon, bicomponent fibers and the like which can be formed into products such as incontinence pads and wound dressings. A mechanical working of the fibers through microcorrugation hinge lines is shown to reduce stiffness in at least one direction without any significant stretching.

A rippling or creping of a surgical dressing is shown by U.S. Pat. No. 3,888,248. The surgical dressing is constructed of an absorbent core which may be creped up to 50% using conventional techniques. The finished product is soft, has greater absorption capacity than gauze and is highly resistant to passing adsorbed fluids back into a wound. Rippling is also disclosed in Canadian Patent Number 974,107 issued on Sep. 25, 1975. In this patent, an elongated sheet of non-woven, randomly arranged, intermingled, short cellulosic fibers and longer reinforcing synthetic fibers are formed into a sheet having an embossed pattern for enhancing the flexibility, absorptive rate and absorptive capacity characteristics of the sheet. The pattern is defined by a plurality of ridges and valleys extending over the entire surface of the sheet with a density of the sheet in the region of the valleys being greater than the density of the sheet in the region of the ridges. U.S. Pat. No. 4,500,585 discloses creping of a non-woven sheet of absorbent composition to make articles which can readily absorb aqueous solutions such as blood, urine and other body exudates.

Similarly, U.S. Pat. No. 5,149,332 discloses an absorbent product which is longitudinally compressed or microcreped to produce microroundulations by compressing the web in its own plane in the direction of its length by compressive forces exerted substantially parallel to a longitudinal direction of the material. The material can also be confined in a small dimension treatment cavity to produce microroundulations. The product is envisioned to be used as superabsorbent assemblages, menstrual tampons, pads such as bandages, compresses, rolls and the like and liquid distributing articles. The product has at least 10 microroundulation per inch in the layer in the direction of treatment.

The use of corrugated materials for medical devices is shown in U.S. Pat. No. 4,608,046 in which a corrugated sheet of alternating ridges and grooves allows ease in rolling or folding the sheet for use as an urinary aid for females by which they may urinate in a standing position.

Embossing to provide various designs is shown in U.S. Pat. No. 3,977,406. In this patent, medical sponges of texturized polyurethane foams are embossed in a pattern composed of a series of continuous lines no more than about 1 inch apart, each line of the design terminating at the edge of a foam sheet and intersecting another line in any direction. The embossed lines are sectioned to flow in a multitude of directions completely and unbrokenly across the sheet allowing the sheet to retain its new folded identify rather than return to its old sheet form. Examples of suitable patterns which may be embossed on the polyurethane foam include squares, rectangles, diamonds, triangles, polygons as well as random non-geometric shaped and designs. The embossed foam can be folded or otherwise compacted for medical usage in a body cavity.

Medical sponges and dressings are used to absorb bodily fluids as blood, serum, spinal fluid, tissue fluid, urine, sweat, bile juice, digestive juices and other fluids. Because the sponge material is difficult to place in human body cavities after it has absorbed fluid and since pre-wetting may decrease the amount of fluid that can be adsorbed, many absorbent sponges and dressing are placed in human body cavities in a dry compressed form.

The reason for mechanical treatment of such dry compressed materials is that the material when compressed into rigid form can cause tissue damage during insertion when encountering an obstacle such as a bony or tissue spur or cavity curve. Furthermore, such rigid sponges can be limited as to depth of insertion and generally do not conform to the wound cavity or body cavity. Foamed absorbent sponges are treated in the aforenoted mechanical manner to allow additional flexibility for packing in cavities, wounds or against organs for maximum absorption.

The present invention utilizes methods which impart flexibility to dry rigid absorbent sponge materials through a number of mechanical sponge treatment techniques to provide a number of novel sponge devices.

SUMMARY OF THE INVENTION

The present invention is directed towards a mechanically softened medical sponge product having a rigid and dry form with high absorptive properties and immediate wicking. The sponge material is mechanically modified with flex lines and/or areas to impart flexibility allowing insertion into body cavities or surgical openings with limited access. This is a continuing need because rigid small devices are required to enter body openings that are difficult to access. Furthermore, if the device is in a wet condition it is difficult to insert and in addition, it compromises absorptive activity of the sponge. Areas of such use occur in the nasal passages which require the need to avoid a bony or tissue spur and protrusions, deviated septums and turbinates; in the otic area to improve placement of ear wick or packing into the tortuous canal without causing tissue damage; and the cervical area with increased ease of placing polyvinyl acetal cervical dilators.

It is one object of the invention that a sponge dressing could be prefolded so that it flexes along the folds and the fold placement predetermined according to the product application. Thus, the folds can be applied on the rigid and dry form of the sponge, when mechanically compressed or expanded according to product application.

It is another object of the invention to provide flexibility to a sponge by perforating the sponge with a series of perforations along certain lines or areas so that specific flexion can be obtained along perforated areas.

Yet another object of the invention is fenestrating to provide random or patterned holes into or through the sponge material thickness, with the hole diameter being a variable of flexing variability. The sponge material flexes along a pattern of holes allowing the dry product to be compressed or expanded according to the product application.

Still another object of the invention provides for the sponges to be incised so that the sponge flexes along the incision or incisions with the incision having a depth, pattern and location according to the product application. Conversely, excising or notching the sponge material allows flexibility along the excisions or removed material areas with the geometry of portions excised as well as their placement being determined according to product application.

It is another object of the invention that the sponge material can also be fabricated with various thicknesses by molding thinner portions to provide flex points with thin and thick portion applications, such as waffling, with alternate lines of thick and thin portions. Also as previously noted, variable compression can be placed on the sponge by site selected compression of the embossing so that different points within the sponge receive between no and complete compression so that the same is embossed in the desired pattern.

In the accompanying drawings, there is shown an illustrative embodiment of the invention from which these and other objectives, novel features and advantages will be readily apparent.

DETAILED DESCRIPTION OF THE DRAWINGS

Figure 1:
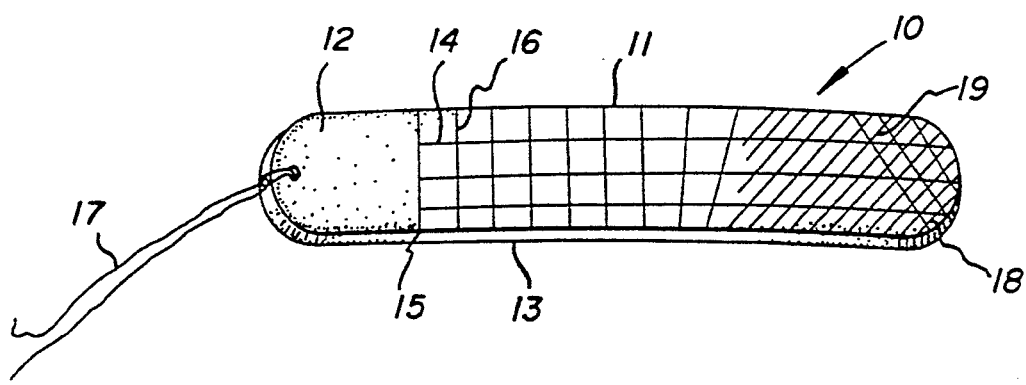
FIG. 1 is a perspective view of the invention showing selective intersecting flex lines of a nasal pack.

The preferred embodiment and best mode of the invention is shown in FIG. 1. As shown in the drawings, a flexible nasal pack 10 is constructed of a solid body 11 of rigid foamed absorbent polyvinyl acetal material with substantially planar sides 13. The material used in the nasal pack is described in U.S. Pat. No. 4,098,728 issued Jul. 4, 1978.

The flexible nasal pack 10 utilizes perforation, incised or excised flex lines to increase flexibility. The distal 2 cm of the pack body 11 form a handle 12 having no flex lines and is strung with a pull thread 17. The lack of flex lines in this area allows the compressed nasal pack 10 to be held and stabilized for creating the flex lines on the main area of the pack. Next to the handle area 12 are located a plurality of horizontal flex lines 14 which run from the end 15 of the handle area 12 along the length of the pack to the proximal end of the pack body. Transverse flex lines 16 intersect the horizontal flex line 14. Angular flex lines 18 are created in the proximal 2 cm of the pack. The angle of flex lines 18 is chosen to provide roughly vertical flexing when the pack 10 is pushed up into the nostril and back in the area of any deviated septum, enlarged turbinate, bony spur or other anatomical abnormality. This angle varies from between 30° and 60° in relation to the axis formed by transverse flex lines 16. A second set of angular flex lines 19 can also be placed perpendicular to the first set of flex lines 18 with the angle varying from 120° and 150°. The flex lines can be perforations, embossing, incised or excised lines. The placement of the flex lines as well as the lack of flex lines insure proper placement.

The nasal pack device 10 is manufactured by cutting the sponge material to the desired shape and compressing same into a rigid body 11 for insertion into the patient's body. The flex lines are created using standard cutting and forming technology. While the invention is described as a nasal pack in the specification, such description should not be construed as limiting its use as the invention is envisioned as also being used as an otic, anal, rectal, laryngeal, pharyngeal, cervical, or vaginal sponge.

Figure 2:
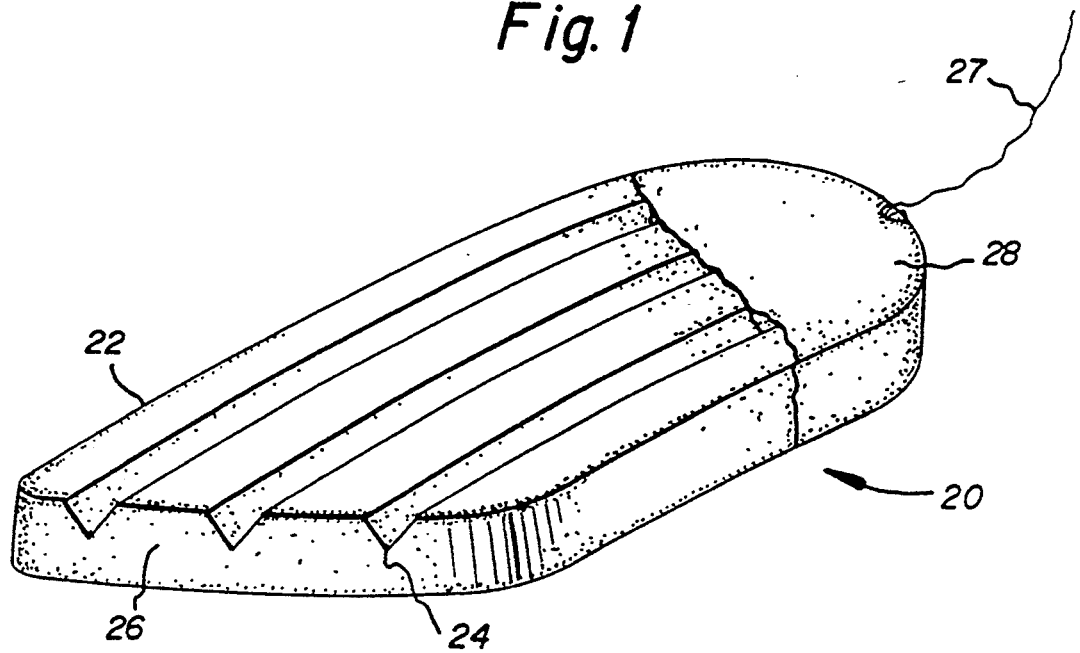
FIG. 2 is a perspective view of another embodiment of a mechanically excised nasal pack according to the invention.
Figure 3:
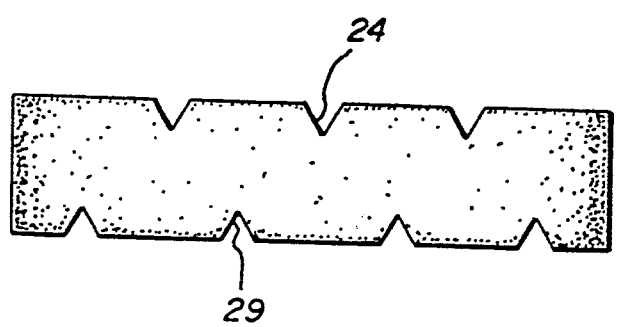
FIG. 3 is a cross sectional view of a modified nasal pack shown in FIG. 2 with staggered excising.

Another nasal pack device 20 as shown in FIGS. 2 and 3 is manufactured as previously noted. It has a plurality of spaced V-shaped notches 24 cut in one side of the body 22 substantially along its length, starting at a point removed from the proximal end 26 and ending at distal end 28 (distal to the patient). A surgical thread 27 is attached to the distal end allowing the nasal pack to be pulled from the cavity after body fluid has been absorbed by the sponge pack. The surgical thread 27 is also used for confirming location of the pack and securing pack placement. Tape can be used to affix the thread to the face of the patient to keep the patient from aspirating the pack. The proximal end 26 of the nasal pack body 22 is constructed with a smooth rounded or bullet shaped configuration. If desired the nasal pack can be notched on both sides as seen in FIG. 3 with either opposing notches opposite notches 24 or staggered notches 29.

The sponge member is constructed of compressed polyvinyl acetal material having a controlled pore size uniformly distributed throughout its volume which is fast wicking and has a high liquid holding capacity. The sponge material has an instantaneous absorbency time and expands uniformly with the capacity to absorb water to the extent of 25 times the sponge weight and has a retained holding capacity of 16 times its own weight as measured by ASTM D-1117-80. The material is marketed under the trademark MEROCEL by the Merocel Corporation.

Figure 4:
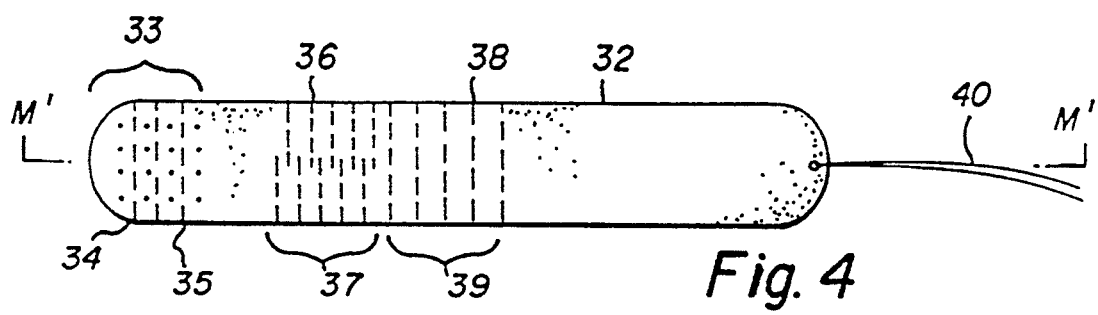
FIG. 4 is a top plan view with perforation flex lines shown partially in phantom of an alternate nasal pack embodiment.
Figure 5:
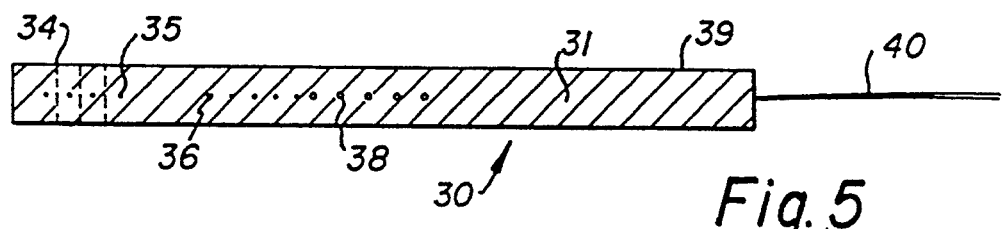
FIG. 5 is an enlarged side elevation view of the embodiment shown in FIG. 4 with perforation flex lines shown partially in phantom.

Yet another nasal pack 30 is shown in FIGS. 4 and 5 in which sequential tunnels, bores or perforations are formed in the nasal pack body 32. This embodiment is constructed of MEROCEL material as previously described.

The nasal pack has an elongated, flat, relatively rigid body 30 curved at both ends and compressed for packaging. The tunnel bores or perforations 34 in the proximal end, first stage 33, are punched into the body 30 and are positioned vertically through the thickness of body 30 with perforations 35 being laterally punched from side to side through the body giving maximum flexibility on the tip of the nasal device 30. In the second stage 37 or midsection of the body, tunnels, bores, or perforations 36 extend into or slightly past the midpoint axis M'—M' of the body from each side. These perforations 36 alternate or are staggered from side 31 to side 32 and extend slightly more than half way through the body past or substantially equal to mid point line M'—M'. In the third stage 39 also in the midsection, tunnel bores or perforations 38 extend from side 31 to side 32 through the nasal pack body 30. The fourth stage or unperforated handle section 39 is not provided with flex lines. If desired, the distal end of the pack body can be provided with a pull thread or cord 40 which is secured via a knot, button, or other protuberance secured in the body of the material at the distal end of the nasal pack. If desired the pull threads can also be secured by tape. While the stages or sections have been discussed in a particular order the stages can be sequenced in a different order and one or more stages can be eliminated as desired.

Figure 6:
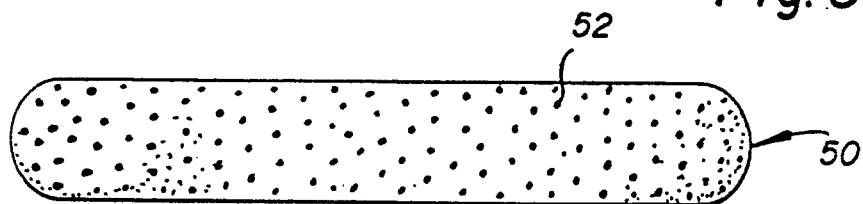
FIG. 6 is a top plan view with random fenestrations of another nasal pack embodiment.

Another mechanically flexed pack embodiment is shown in FIG. 6. In this embodiment, a flexible sponge 50 is provided with random fenestrations 52. It will be appreciated that these fenestrations can be angled with respect to the plane of the surface or made perpendicular to the plane of the surface. These fenestrations can be made partial depth or through the sponge thickness along a portion or all of the sponge surface. The fenestrations cross-sectional area and proximity to other fenestrations affect the degree of resultant flexibility.

Figure 7:
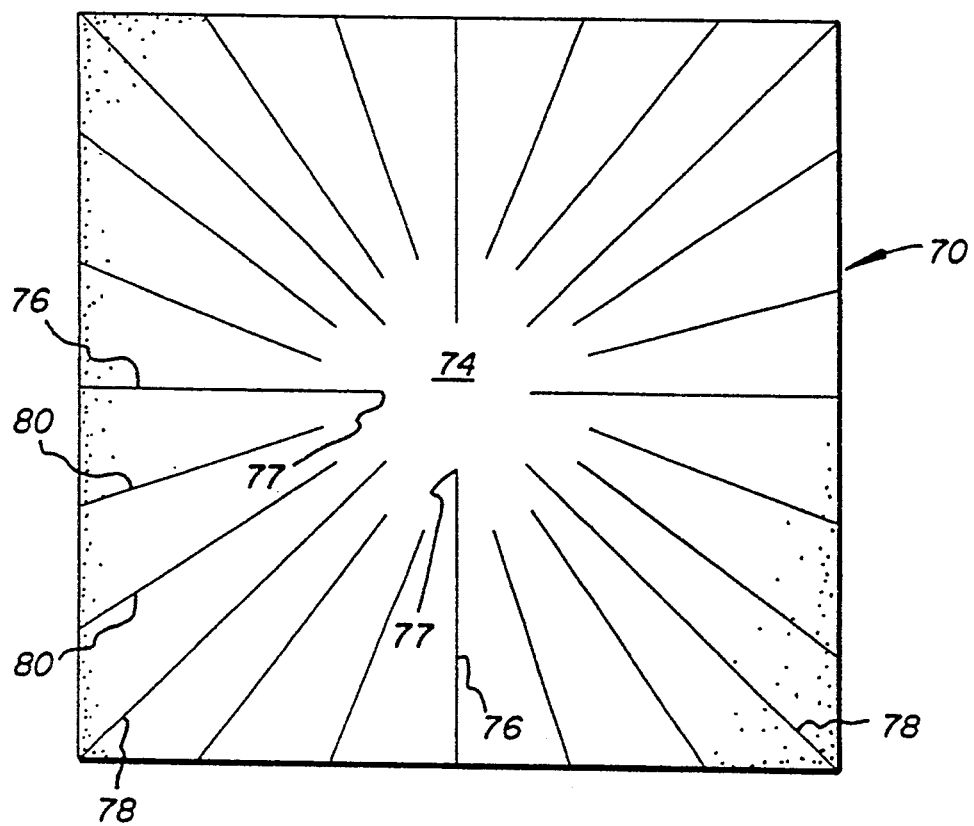
FIG. 7 is a top plan view of still another embodiment of a surgical sponge dressing having perforation flex lines to enhance flexibility.

Another mechanically flexed sponge dressing embodiment is shown in FIG. 7. In this device, a 4"×4"×¼" thick sponge dressing body 70 is used with a number of radiating flex lines. The polyvinyl acetal sponge is made of MEROCEL ® material with a uniform pore size ranging from commercial product designated Merocel CF-50, CF-150, CF-200 and CF-400 for insertion into open wounds. The sponge can have a pore size ranging from <0.05 mm to about 1.0 mm as determined by a stereoscopic microscope eyepiece. The sponge dressing 70 has an instantaneous absorbency time and expands uniformly with the capacity to absorb water to the extent of 25 times the sponge weight and has a retained holding capacity of 16 times its own weight as measured by ASTM D-1117-80. If desired, the length, width and thickness of the wound dressing can vary. The dressing can be packaged sterile and dry or pre-moistened in a sterile peel pouch. In the case of incising the flex lines to a partial depth, the same design would be done on the reverse side. The present embodiment has a central portion 74 which is adapted to be placed over a heel ulcer and outer periphery of the dressing constructed to be collapsed by folds or partial folds at the flex lines. If desired, entire portions of the dressing 70 can be folded over onto itself forming a double thickness extension which can be trimmed off. Alternatively, the dressing can be folded or otherwise layered for insertion into a cavity wound.

Thus, it can be seen that four flex lines 76 having a perpendicular axis which form the 3, 6, 9, and 12 positions as viewed from the face of a clock extend towards the center or midpoint of mechanically unflexed area 74. A secondary series of flex lines 78 extend on an axis from the corners of the square pad toward the midpoint of the square. These flex lines extend inward slightly less than circumference of the non-treated area 74 as delineated by an arc joining the inner end points 77 of flex lines 76. Two or more secondary flex lines 80 are formed in the sponge material between flex lines 76 and 78 and terminate at a greater end point distance away from the midpoint than the flex line 78, thus allowing easy folding and flexibility.

It is also envisioned that at least flex lines 76 and 78 can alternately be formed in the dressing by prefolding the body along these lines to form flex lines of compaction and expansion in the material.

It should be noted that flex lines as used in this application can mean lines formed by perforation, fenestrating, incising, excising, embossing, or molding with thinner line areas.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. A medical sponge, comprising a sterile rigid absorbent linearly shaped sponge body, one end of said body being rounded, a plurality of parallel flex lines formed in said linear body running substantially along its length, one section of said body having flex lines formed therein running perpendicular to and intersecting said parallel flex lines, and an end of said body being provided with angular flex lines formed therein running angularly to and intersecting said parallel flex lines.

2. A medical sponge as claimed in claim 1 wherein said flex lines are perforations.

3. A medical sponge as claimed in claim 1 wherein said flex lines are incised.

4. A medical sponge as claimed in claim 1 wherein said flex lines are embossed.

5. A medical sponge as claimed in claim 1 wherein said flex lines are excised.

6. A medical sponge as claimed in claim 1 wherein said medical sponge is a nasal pack.

7. A medical sponge as claimed in claim 1 wherein said medical sponge is an otic pack.

8. A medical sponge as claimed in claim 1 wherein said medical sponge is an anal pack.

9. A medical sponge as claimed in claim 1 wherein said medical sponge is a rectal pack.

10. A medical sponge as claimed in claim 1 wherein said medical sponge is a laryngeal pack.

11. A medical sponge as claimed in claim 1 wherein said medical sponge is an orthopedic pack.

12. A medical sponge as claimed in claim 1 wherein said medical sponge is a pharyngeal pack.

13. A medical sponge as claimed in claim 1 wherein said medical sponge is a cervical pack.

14. A medical sponge as claimed in claim 1 wherein said medical sponge is a vaginal pack.

15. A medical sponge comprising a rigid absorbent linearly shaped sponge body, at least one end of said body being rounded, a plurality of parallel flex lines formed in said linear body running along its length, a plurality of flex lines formed in said body running perpendicular to and intersecting said parallel flex lines, said body being additionally provided with angular flex lines formed therein running angularly to and intersecting said parallel flex lines and an end of said body provided without flex lines forming a handle for the medical sponge.

16. A medical sponge comprising a rigid absorbent linearly shaped sponge body, one end of said body having a section with no flex lines, a plurality of parallel flex lines formed in said linear body running along its length from the unflexed section, an adjacent section of said body being provided with flex lines running transverse to said parallel flex lines, and an end of said body being provided with angular flex lines running angularly from 30 degrees to 60 degrees from said transverse flex lines forming an end of said medical sponge.

17. A medical sponge as claimed in claim 16 wherein said angular flex lines form a section of about 2 cm.

18. A medical sponge comprising a rigid absorbent linearly shaped sponge body, one end of said body being provided with a plurality of flex lines running transverse its length and through its thickness, a second section of said body provided with a plurality of staggered flex lines running substantially along its width, said staggered flex lines terminating around the midpoint linear axis of the sponge body, a third section of said body provided with plurality of parallel flex lines running through its width, and a section including the other end of said body which has no flex lines and serves as a handle.

19. A medical sponge as claimed in claim 18 wherein said flex lines are incised.

20. A medical sponge as claimed in claim 18 wherein said flex lines are a plurality of bores in said body.

21. A medical sponge comprising a sterile rigid absorbent linearly shaped sponge body, said body being provided with a plurality of staggered flex lines running into said body from opposing sides, said staggered flex lines being positioned substantially parallel to each other with the ends of said staggered flex lines terminating near a central midpoint linear axis of the body.

22. A medical sponge as claimed in claim 21 wherein said body is additionally provided with a plurality of throughgoing flex lines running through a width and a height of said body transverse to each other.

23. A medical sponge as claimed in claim 21 wherein said body is additionally provided with a plurality of parallel flex lines running through its width from side to side.

24. A medical sponge comprising a rigid absorbent linearly shaped sponge body with substantially planar sides, one end of said body provided with a plurality of flex lines formed by a plurality of linear orientated perforations running transverse its length and through its thickness, a section of said body provided with a plurality of staggered flex lines running staggered from side to side and extending about halfway through said body and a section of said body provided with plurality of parallel flex lines running through its width from side to side, and a section including the other end of said body which has no flex lines and serves as a handle.

* * * * *